United States Patent
Ferreira et al.

(12) 
(10) Patent No.: US 6,664,297 B1
(45) Date of Patent: Dec. 16, 2003

(54) METHODS FOR INHIBITION AND DISSOLUTION OF AMYLOIDOSES BY ADMINISTRATION OF COMPOSITIONS COMPRISING 2,4-DINITROPHENOL

(75) Inventors: Sergio Teixeira Ferreira, Rio de Janeiro (BR); Fernanda Guarino De Felice, Rio de Janeiro (BR); Paulo Roberto Ferreira Louzada, Jr., Rio de Janeiro (BR)

(73) Assignee: Universidade Federal do Rio de Janeiro (BR)

( * ) Notice: Subject to any disclaimer, the term of this patent is extended or adjusted under 35 U.S.C. 154(b) by 0 days.

(21) Appl. No.: 09/692,743

(22) Filed: Oct. 18, 2000

(51) Int. Cl.[7] .................. A61K 31/045; A61K 31/04; A01N 33/18; A01N 33/24; A01N 31/08
(52) U.S. Cl. ................ 514/728; 514/724; 514/727; 514/731; 514/742
(58) Field of Search ................. 514/728, 724, 514/727, 731, 742

(56) References Cited

U.S. PATENT DOCUMENTS 5,488,145 A    1/1996   Carney ................ 562/62

FOREIGN PATENT DOCUMENTS

WO    WO 97/44020    * 11/1997
WO    WO 99/20601      4/1999    ......... C07C/291/02

OTHER PUBLICATIONS

Hardman et al., ED., Goodman and Gilman's The Pharmacological Basis of Therapeutics, 9th Ed., 1996, p. 513.*

De Felice, F.G., et al., "Characterization of Compounds that Prevent Aggregation and Neurotoxicity of Alzheimer's Disease Aβ Peptide." Biophysical Journal, vol. 78, (2000) pp. 289a (abstract).

* cited by examiner

*Primary Examiner*—Sreeni Padmanabhan
*Assistant Examiner*—Michael A Willis
(74) *Attorney, Agent, or Firm*—Fish & Richardson P.C.

(57) ABSTRACT

The inhibition of the formation and development of amyloidoses, as well as the dissolution of amyloidoses in organisms is claimed. Methods for the diagnosis of amyloidoses using aromatic and heteroaromatic compounds having at least one electron-withdrawing groups are claimed.

12 Claims, 6 Drawing Sheets

(3 of 6 Drawing Sheet(s) Filed in Color)

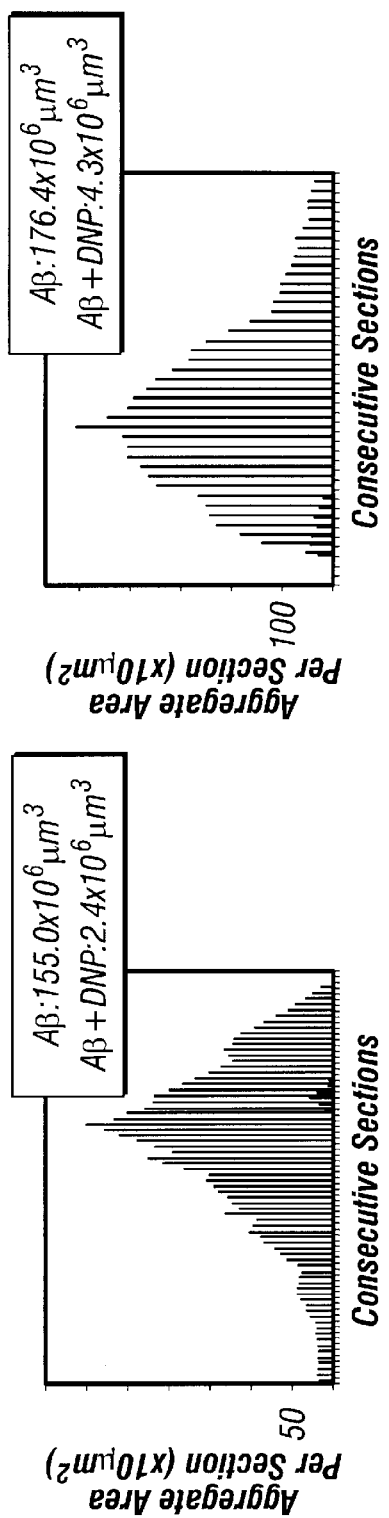
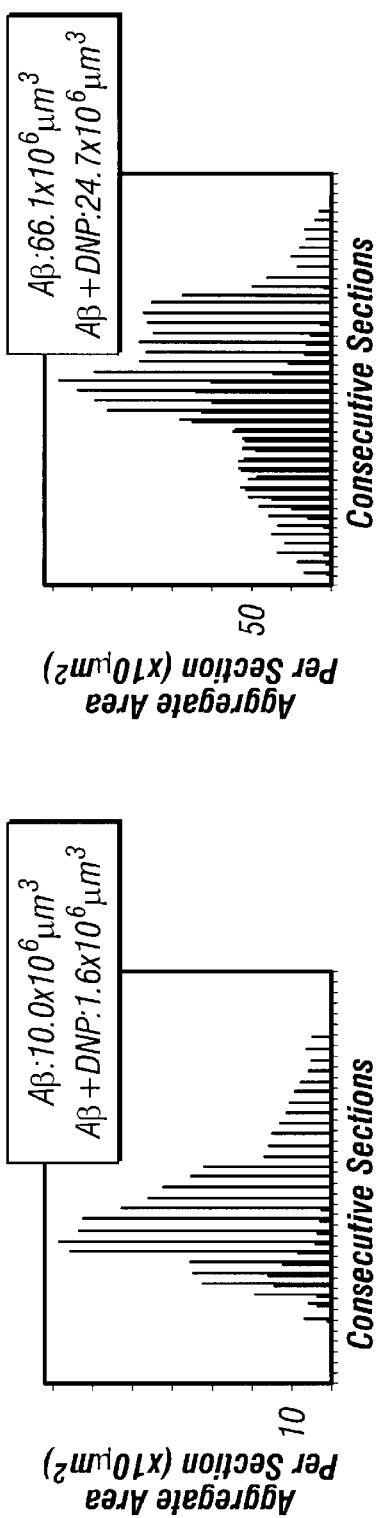
FIG. 5B
FIG. 5C
FIG. 5D
FIG. 5E

METHODS FOR INHIBITION AND DISSOLUTION OF AMYLOIDOSES BY ADMINISTRATION OF COMPOSITIONS COMPRISING 2,4-DINITROPHENOL

CROSS-REFERENCE TO RELATED APPLICATION

This application claims the benefit of Brazilian Patent Application No. PI9904931-7, Filed Oct. 18, 1999.

FIELD OF THE INVENTION

The invention relates to the inhibition of formation of potential amyloidoses, the inhibition of development of existing amyloidoses, and the dissolution of existing amyloidoses, by the administration of particular compounds and compositions comprising such compounds.

BACKGROUND

Amyloidoses are pathological conditions characterized by the presence of amyloid deposits. Currently a number of amyloidogenic proteins or peptides (derived from different precursor molecules) are known to be involved in diseases as diverse as diabetes, rheumatoid arthritis, Alzheimer's disease, and others. The elimination of factors that promote the formation or development of amyloid deposits can result in the loss of existing deposits and the functional recovery of the affected tissues (Kisilevsky et al., *Crit. Rev. Biochem. Mol. Biol.*, 32, 361–404, 1997).

U.S. Pat. No. 5,859,001 describes compositions and methods for protecting against the death of central nervous system cells and also relates to the stimulation of neuronal survival in individuals with neurodegenerative conditions. According to this patent, neuroprotection can be provided to a cell population via the use of non-estrogenic compounds having a terminal phenol group in a structure which contains at least one additional ring and with a molecular weight which is less than 1000 Daltons.

U.S. Pat. No. 5,854,215 describes a method to inhibit the aggregation of natural β-amyloid peptides, including exposing the natural β-amyloid peptide to modulating compounds such that the aggregation of the β-amyloid peptide can be inhibited. The modulating compounds are β-amyloid peptides which have been modified on their amino terminal group.

U.S. Pat. No. 5,840,294 describes a method for the inhibition of amyloid deposition, the method including administering a compound containing an anionic sulfonate group in an amount sufficient to inhibit the interaction between an amyloidogenic protein and a basal membrane constituent. The carrier molecule to which the anionic sulfonate group is attached can be a polymer, a peptide, a peptidomimetic, an aliphatic group, a cycloalkyl group, a heterocyclic group or some combination.

The publications WO 97/16191 and WO 97/16194 relate to the inhibition of amyloid aggregation in mammals via the administration of naphthylazo or 9-acridinone derivatives.

There is currently no specific treatment available for amyloidogenic diseases involving clinically approved drugs that inhibit the formation or development of existing amyloid deposits, or that cause the dissolution of existing amyloid deposits.

After clinical diagnosis of the disease, patients are usually submitted to treatments that are directed towards some of the symptoms associated with the disease. These treatments include, among others, the administration of acetylcholinesterase inhibitors, which act to raise the concentration of the neurotransmitter acetylcholine. Acetylcholine is present at reduced levels in patients with Alzheimer's disease. Other forms of treatment include the use of anti-oxidants, such as vitamins A, C and E, in an attempt to improve the antioxidant properties of the neurons.

There appear to be several pre-requisites for amyloidogenesis in vivo (Kisilevsky, *Nature Medicine*, 4(7), 772–773, 1998). These include: minimal concentrations of protein or peptide precursor; the presence of a seed or aggregation nucleus; additional components which bind to the amyloid peptide; self-interaction of amyloid peptides and/or interaction with other molecules; and failure of particular amyloid deposit removal mechanisms. The inhibition of the proteolytic processing of the amyloid protein precursor giving rise to the β-amyloid peptide might lead to a reduction in the amyloid peptide concentration, and has been proposed as a possible therapeutic strategy (Higaki et al., *J. Neurochem.*, 68(1), 333–6, 1997; Xu, H. et al., *Nature Medicine*, 4(4), 447–451, 1998).

Soto et al. (*Nature Medicine*, 4(7), 882–6, 1998) have proposed the use of peptides which destabilize β-sheets as anti-fiber forming agents and blockers of the in vitro neurotoxicity of Aβ. The principal problems with the use of peptides as potential therapeutic agents for Alzheimer's disease arise from the fact that peptides are targets for proteolytic degradation and, as a general rule, present low permeability across the blood-brain barrier. These difficulties therefore limit their pharmaceutical applications.

Therefore, as can be seen from the state of the art, no specific treatment for amyloidogenic diseases exists. The therapeutic approaches include, for example, methods for improving cholinergic transmission, the use of antioxidants, and attempts to administer trophic factors.

None of the approaches presented up to this point directly attacks or has any effect on the molecular causes of the disease, i.e., the formation of amyloid deposits and amyloid plaques.

SUMMARY OF THE INVENTION

A method for the inhibition of amyloidoses by administering particular compounds is disclosed herein. More specifically, a method for the treatment and diagnosis of diseases caused by amyloidoses, particularly Alzheimer's disease, is disclosed, as well as pharmaceutical compositions for inhibition of amyloidoses.

According to the invention particular compounds impede the aggregation of amyloid fibers composed of the β-amyloid peptide, and impede the in vitro neurotoxicity of the β-amyloid peptide or of fibers composed of this peptide. Furthermore, with the aid of a model system of cerebral amyloid deposition, it is shown that aromatic and heteroaromatic compounds as described herein can cause a marked reduction in the volume occupied by amyloid deposits, for example, in the hippocampi of rats.

In one aspect, a method for the treatment and/or prevention of amyloidogenic diseases employing particular compounds is presented.

In another aspect, a pharmaceutical composition for use in individuals suffering from amyloidogenic diseases, particularly Alzheimer's disease, employing particular compounds is presented.

In yet another aspect, a useful compound to be employed in the development of a pharmaceutical composition for use in individuals suffering from amyloidogenic diseases, particularly Alzheimer's disease, is presented.

In yet still another aspect, a method to diagnose the deposition of amyloid aggregates, and, consequently, detect pathological conditions associated with amyloid aggregation, such as Alzheimer's disease, is presented.

As used herein, "amyloid" refers to extracellular protein deposits that are found in a series of different diseases. As used herein, the term "therapeutically effective" means that quantity of the aromatic or heteroaromatic compounds described herein which inhibit amyloidosis without causing unacceptable toxic effects. As used herein, the term "pharmaceutically acceptable carrier" includes an ingredient which is compatible with, and stable when in the presence of, the aromatic or heteroaromatic compounds described herein, and is employed in oral or parenteral formulation, for example, for the intravenous or intramuscular administration of the composition.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entireties. In case of conflict, the present specification, including definitions, will control. In addition, the materials, methods, and examples are illustrative only, and not intended to be limiting.

Other features and advantages of the invention will be apparent from the following detailed description, and from the claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 5B–5E are plots showing quantitative analysis of the area of amyloid deposits in consecutive hippocampal sections of rat brains treated or not with 2,4-dinitrophenol.

DETAILED DESCRIPTION

Figure 1A:
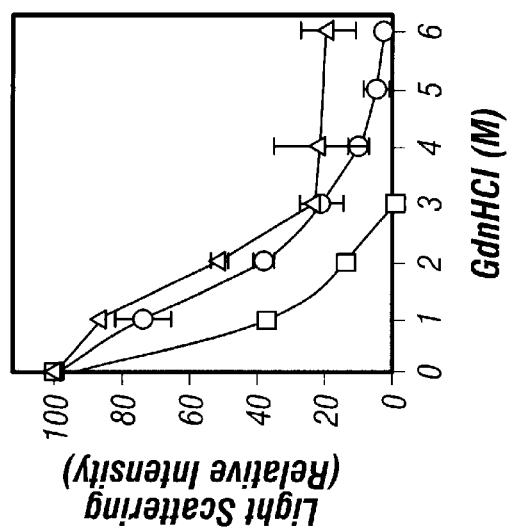
FIG. 1A is a plot of light scattering intensity as a function of guanidine HCl concentration and peptide chain length.

Although they vary in occurrence, all amyloid deposits possess common morphological and histological properties, such as, for example, staining with specific dies, for example Congo Red, and possess a red-green birefringent appearance under polarized light after staining. These deposits also share ultra-structural features in common, as well as X-ray diffraction and infrared spectroscopic properties.

Alzheimer's disease (AD), described for the first time by the physician Alois Alzheimer in 1906, is a progressive neurological disorder. The clinical symptoms of AD include a progressive deterioration in cognitive functions, severe loss of memory and finally total dementia. AD affects from 5 to 11% of the population under 65 years of age and more than 47% of the population over 85 years of age.

Pathologically, AD is characterized by the presence of distinct cerebral lesions in patients. These cerebral lesions include abnormal intracellular filaments (neurofibrillary tangles, NFTs) and extracellular deposits of amyloidogenic proteins in senile or amyloid plaques. The amyloid deposits, or amyloid plaques, are also present in the walls of blood vessels of the brains of patients affected with AD.

The principal protein constituent of the amyloid plaques has been identified as a peptide of approximately 4 kiloDaltons (39 to 43 amino acid residues), denominated β-amyloid peptide (Glenner et al., *Biochem. Biophys. Res. Commun.*, 120,:885–890, 1984); Masters, et al., *Proc. Natl. Acad. Sci. USA*, 82, 4245–4249, 1985). Diffuse deposits of β-amyloid peptide are frequently observed in the brains of normal adults, while the brain tissue of patients with AD is characterized by the presence of amyloid plaques which present a dense and compact nucleus. These observations suggest that the deposition of β-amyloid peptide contributes to the neuronal destruction which occurs in AD.

The β-amyloid peptide is directly related to Alzheimer's disease and Down's Syndrome. Accumulation of these 4 kiloDalton peptides in the brain is due to the cleavage of a precursor protein, denominated Amyloid Precursor Protein (APP). The amino terminal residue of Aβ is frequently an aspartic acid (Asp), suggesting that a protease which cleaves between the methionine (Met) at position 596 and Asp at position 597 of APP generates a fragment which corresponds to the amyloid peptide.

The compounds useful for the disclosed methods are characterized by the presence of an aromatic or heteroaromatic compound. Aromatic or heteroaromatic compounds which are substituted as described herein include benzene, naphthalene, anthracene, and similar hydrocarbon aromatics. Biphenyl-derivatives are also contemplated as useful in the methods and compositions described herein. Heteroaromatic compounds include nitrogen-containing aromatic compounds such as pyrrole, pyridine, as well as heteroaromatic compounds containing more than one nitrogen atom. Other heteroarormatic compounds include oxygen-containing aromatic compounds such as furan, as well as heteroaromatic compounds containing more than one oxygen atom. Other heteroaromatic compounds include sulfur-containing aromatic compounds such as thiophene, as well as heteroaromatic compounds containing more than one sulfur atom. Other aromatic systems including both hydrocarbon- and heteroatom-aromatic rings can be used, for example, indole, quinoline, isoquinoline and other systems with hydrocarbon- and heteroatom-aromatic rings fused or bridged together.

The aromatic or heteroaromatic compounds are substituted with at least one electron-withdrawing group. Electron-withdrawing groups can include, for example, hydroxy; nitro; primary, secondary or tertiary amino, such as $C_{1-4}$ mono- or $C_{1-4}$ dialkylamino, mono- or diarylamino, or $C_{1-4}$ alkyl aryl amino; ammonio, such as $C_{1-4}$ mono-, di- or trialkylammonio, mono-, di- or triarylammonio, or ammonio groups having any combination of N—$C_{1-4}$ alkyl or N-aryl substituents; halo; $C_{1-4}$ alkoxy; aryloxy; cyano; isocyano; mercapto; $C_{1-4}$ alkylthio; arylthio; sulfino; $C_{1-4}$ alkylsulfonyl; arylsulfonyl; carboxy; $C_{1-4}$ alkoxycarbonyl; aryloxycarbonyl; $C_{1-4}$ alkylcarbonyl; or arylcarbonyl.

The aromatic or heteroaromatic compounds have at least one such electron-withdrawing group. Such compounds may have two, three or more such electron-withdrawing groups. For example, the compound can be nitrobenzene, phenoxybenzene, cyanobenzene, aminonaphthalene, nitronaphthalene, nitropyridine, aminopyrrole, bromofuran, and other similar compounds which will be recognized as fitting this description by one of skill in the art. Such one electron-withdrawing group-containing compounds may be further substituted with other, non-electron-withdrawing groups, such as, for example, alkyl, aryl and other like groups. Thus, the compounds can be alkylphenols, alkylnitrobenzenes, and the like.

There can be two electron-withdrawing groups which are the same or different, so that the compound can be a nitrophenol, a dinitrobenzene, a dialkoxybenzene, a nitroaniline, a nitroanisole, a bromonitrobenzene, an aminophenol, an aminoaniline, an aminoanisole, an aminobromobenzene, a nitrochlorofuran, an aminobromothiophene, and other combinations which will be recognized as fitting this description by one of skill in the art. The substitution pattern on benzene can be ortho-, meta-, or para-, and the substitution pattern on other aromatic or heteroaromatic compounds is similarly variable. Such two electron-withdrawing group-containing compounds may be further substituted with other, non-electron-withdrawing groups, such as, for example, alkyl, aryl and other like groups. Thus, the compounds can be, for example, alkylnitrophenols, dialkylnitrophenol, alkylarylnitrophenols, arylhydroxyanilines, and the like.

There can be three electron-withdrawing groups which are the same or not the same, so that the compound can be a dinitrophenol, a diaminophenol, an aminonitrophenol, a dialkoxyphenol, a nitroalkoxyphenol, a dihalophenol, a dihydroxynitrobenzene, a dihydroxyaniline, a dinitrohydroxynaphthalene, a diaminohydroxynaphthalene, and other similar compounds which will be recognized as fitting this description by one of skill in the art. The substitution pattern of such three electron-withdrawing group-containing compounds is also variable. Such three electron-withdrawing group-containing compounds may be further substituted with other, non-electron-withdrawing groups, such as, for example, alkyl, aryl and other like groups. Thus, the compounds can be, for example, dinitroalkylphenols, arylalkylnitrophenols, and the like.

The compounds described herein are desirably sufficiently soluble in water or substantially aqueous media to form solutions in such media. These water-soluble molecules are desirably hydrophobic enough to cross the blood-brain barrier and gain access to the CNS. The compounds are also desirably not substantially toxic to organisms to which the compounds are to be administered.

In particular embodiments, the compounds are 2,4-dinitrophenol, 3-nitrophenol, 2-amino-4-nitrophenol, 2-amino-5-nitrophenol, 3,4-dimethylphenol, 4-nitrophenol, 4-aminoanisole, 4-nitrobromobenzene, 4-bromophenol, 4-chlorophenol, 3-nitrophenol, 2-amino-4-chlorophenol, 2,4-dinitroanisole, 3-nitroanisole, 2-nitro-4-aminophenol, 2-amino-4-nitroanisole, 2-amino-5-nitroanisole, 2-nitro-4-aminoanisole, or 4-nitrophenol.

In accordance with one of the objects of the present invention, the method for the treatment and/or prevention of amyloidogenic diseases includes impeding the formation of amyloid fibers or dissolving existing fibers in mammals, via the administration to a mammal of a therapeutically effective quantity of the aromatic or heteroaromatic compounds described herein or their pharmaceutically acceptable salts.

According to another object of the present invention, a pharmaceutical composition for use in individuals suffering from amyloidogenic diseases includes (a) a therapeutically effective quantity of aromatic or heteroaromatic compounds described herein; and (b) a pharmaceutically acceptable carrier. Adequate pharmaceutically acceptable carriers for use according to the present invention may be, for example, common diluents or excipients, such as starch, sugar, talc or similar substances, in the form of tablets, capsules, pills, syrups, suspensions or similar formulations. For parenteral use, the compounds are, preferentially, dissolved in isotonic saline or glucose solution for injection or intravenous administration. The quantity typically used in the compositions of the present invention may vary from about 0.1 to about 100 mg/day.

Because the compounds of the present invention possess the capacity to bind to amyloid, the present invention further presents a method for diagnosing the deposition of amyloid aggregates, and, consequently, detecting pathological conditions associated with amyloid aggregation, such as Alzheimer's disease. This method includes administering a therapeutically effective quantity of radiolabeled aromatic or heteroaromatic compound as described herein, or its pharmaceutically acceptable salt, to a mammal in similar fashion to that described above for non-radiolabeled compounds. The mammal is then subjected to a radiodetection analysis such as, for example, scintillography, to detect the deposition of amyloid aggregates.

The invention will be further described in the following examples, which do not limit the scope of the invention described in the claims.

EXAMPLES

The capacity of the aromatic or heteroaromatic compounds described herein to inhibit amyloidoses was determined by representative assays presented below, for which phenolic derivatives were used.

Two aspects can be used to demonstrate the characterization of the efficacy of the exemplified phenolic derivatives. A first aspect is the characterization of phenol derivatives as anti-amyloidogenic agents, which impede the formation of potential amyloid fibrils and cause dissolution of existing fibrils. A second aspect is the demonstration of protective effects of the phenol derivatives against neurotoxicity induced by β-amyloid peptide in vitro.

Investigations of factors involved in and/or determinants of the stability of amyloid aggregates of β-amyloid peptide from Alzheimer's disease were carried out. The formation of β-amyloid peptide aggregates was followed under diverse experimental conditions by 90° light scattering intensity measurements and by transmission electron microscopy analysis.

Figure 1B:
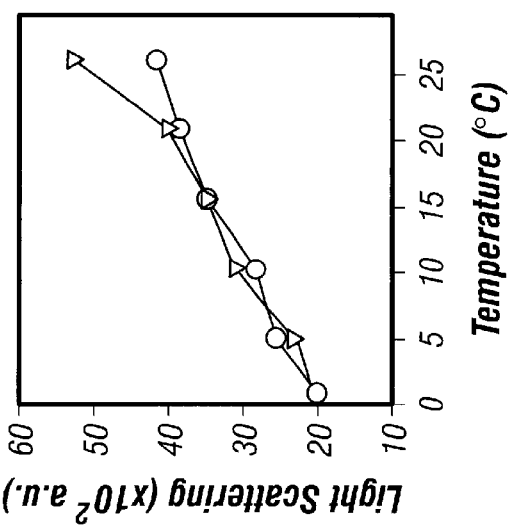
FIG. 1B is a plot of light scattering intensity as a function of temperature.

Aβ peptides of different chain-lengths (Bachem Inc., Torrance, Calif., USA) were freshly dissolved from lyophilized powder in 50% (v/v) trifluoroethanol (TFE) in PBS. Aggregation was triggered by dilution of aliquots from the stock solution into PBS (resulting in ≦0.5% (v/v) residual TFE), and was followed as a function of time by light scattering measurements. Light scattering was measured in sealed cuvettes at 500 nm on ISS Inc. (Champaign, Ill., USA) PC1 or Hitachi F-4500 spectrofluorometers. Except as indicated in FIG. 1B, all measurements were carried out at 23° C. Low temperature experiments were performed using a thermostated cell holder and flushing the cell compartment with $N_2$ to avoid condensation. All results shown represent equilibrium light scattering values obtained for each sample.

Aggregated samples were also examined by transmission electron microscopy. In this case, Aβ (22 μM) was incubated in PBS in the absence or in the presence of nitrophenols, as indicated. After 48 hours, samples were stained with 1% uranyl acetate.

Concentrated peptide stock solutions were prepared in 50% (v/v) trifluoroethanol. Aggregation was triggered by dilution in phosphate-buffered saline (PBS) and was followed by means of light-scattering measurements (FIGS. 1A, 1B, 1C), thioflavin T fluorescence (not shown) and electron microscopy (FIG. 2). Equilibrium light scattering values were used as an index of the extent of aggregation under different experimental conditions.

The stability of the aggregates was initially measured at different temperatures, within a range varying from 1 to 80° C., in the presence or absence of the chaotropic agent guanidine hydrochloride, at concentrations which were varied from 0 to 6 M, and by using β-amyloid peptides of varying amino acid chain lengths. The amino acid chain lengths varied between peptides containing 28, 42 or 43 amino acids, and are referred to as Aβ1-28, Aβ1-42 and Aβ1-43, respectively. These three types of synthetic β-amyloid peptide are commercially available, and, in the present case, were obtained from Bachem Inc. (USA).

Confirmation that the light scattering intensity measurements were in fact related to the formation of amyloid fibrilar aggregates was made by transmission electron microscopy analysis using uranyl acetate staining.

Example 1
Aggregate Stability

Stabilities of the fibrillar amyloid aggregates of peptides $Aβ_{1-28}$, $Aβ_{1-42}$ and $Aβ_{1-43}$ in the presence of guanidine hydrochloride were compared. Measurements of the reduction in light scattering intensity as a function of the concentration of guanidine hydrochloride were used as an index of amyloid aggregate dissolution. The disaggregation of Aβ (10 μM) by GdnHCl is shown in FIG. 1A. Samples were incubated for 1 hour in the presence of the indicated concentrations of GdnHCl prior to measurements. Different symbols correspond to $Aβ_{1-28}$ (□), $Aβ_{1-42}$ (O) and $Aβ_{1-43}$ (Δ), and represent averages±S.D. from 3–5 determinations.

The aggregation of $Aβ_{1-42}$ and $Aβ_{1-43}$ was very fast, and was essentially complete within a few minutes after dilution in phosphate-buffered saline (PBS), whereas aggregation of $Aβ_{1-28}$ was quite slow (for example, 10–12 days). Interestingly, we found that the stability of fibrillar Aβ in guanidine hydrochloride (GdnHCl) solutions was markedly dependent on peptide chain length (FIG. 1A). For $Aβ_{1-28}$, complete disaggregation was obtained at 3 M GdnHCl, whereas full disaggregation of $Aβ_{1-42}$ required 5–6 M GdnHCl.

The results indicated that the amyloid aggregates formed by peptides Aβ1-42 and Aβ1-43 were significantly more resistant to dissolution by guanidine hyrdochloride than the amyloid aggregate formed by peptide Aβ1-28.

Example 2
Aggregate Characterization as a Function of Temperature

The cold disaggregation of $Aβ_{1-42}$ is shown in FIG. 1B. The sample was initially aggregated at 25° C., and progressively cooled to the indicated temperatures (circles). Light scattering intensities were acquired after 20 min equilibration at each temperature. Triangles represent scattering intensities measured upon re-heating the sample to room temperature, and indicate the reversibility of the cold-disaggregation process. The stabilities of the amyloid aggregates formed by the β-amyloid peptides were characterized as a function of temperature within a range varying from 1 to 80° C. It was shown that a reduction in temperature, within the range from 1 to 25° C., resulted in a reversible dissolution of amyloid aggregates previously formed at 25° C.

Decreasing temperature from 25° C. to 1° C. caused reversible and nearly complete disaggregation of Aβ (FIG. 1B). Low temperatures lead to destabilization of hydrophobic interactions, by decreasing the entropic contribution to the hydrophobic effect. Thus, these results indicate that a significant contribution to the stability of Aβ aggregates comes from entropy-driven hydrophobic interactions.

Example 3
Examination of the Amino Acid Sequences

Examination of the amino acid chain sequences corresponding to the peptides Aβ1-28, Aβ1-42 and Aβ1-43 revealed that all of the charged and polar amino acids in these peptides reside in the sequence between amino acids 1 and 28, while the sequence between amino acids 29 and 42 (or 43) contains only non-polar amino acids. Residues 29–42 comprise a cluster of non-polar amino acids contained in a transmembrane sequence of APP.

The examination of the amino acid sequences together with the above-described data shows that the carboxy-terminal region of the peptides, between amino acids 29 and 42/43, is important for the stability of the amyloid aggregates, possibly via its capacity to stabilize non-polar interactions between β-amyloid peptide molecules.

Based on these results, drugs with chemical characteristics and favorable solubilities for interaction with β-amyloid peptide were tested aiming at destabilizing the amyloid aggregates. The aromatic and heteroaromatic compounds described herein showed themselves to possess sufficiently apolar character to permit their interference with the non-polar interactions described above as important for the stability of the amyloid aggregates.

On the other hand, the aromatic and heteroaromatic compounds described herein are sufficiently soluble in water or substantially aqueous media to allow for their possible pharmaceutical use and for in vitro assays with neuron cultures.

Example 4
Assays

One class of compounds we tested were the nitrophenols. The disaggregation of $Aβ_{1-42}$ by nitrophenols was determined. 3-nitrophenol (NP; O) or 2,4-dinitrophenol (DNP; □) were added to aggregated samples prepared as described above. Light scattering intensities were measured 1.5 hour after addition of the drugs. Symbols represent averages±S.D. from 3 experiments.

Figure 1C:
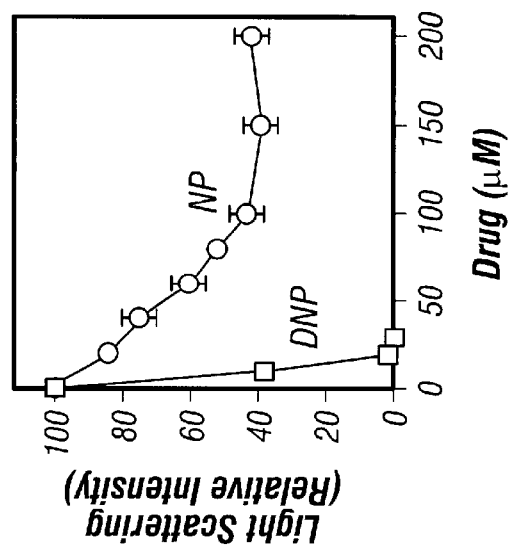
FIG. 1C is a plot of light scattering intensity as a function of aromatic or heteroaromatic compound concentration.
Figure 2:
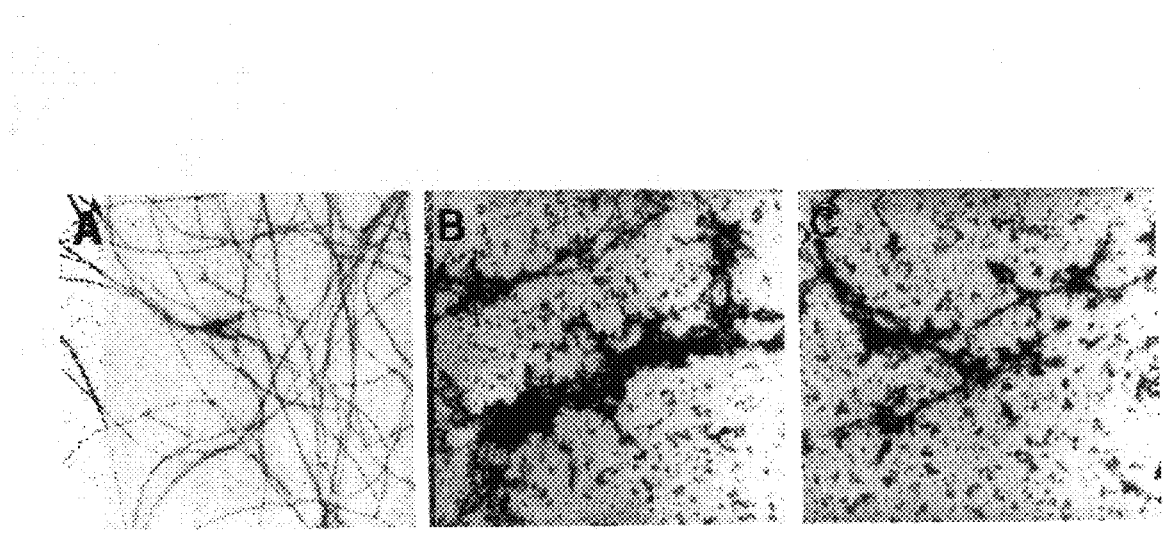
FIG. 2A is an electron micrograph of a control sample of fibrillar β-amyloid peptide.
FIG. 2B is an electron micrograph of β-amyloid peptide treated with 3-nitrophenol.
FIG. 2C is an electron micrograph of β-amyloid peptide treated with 2,4-dinitrophenol.

Addition of micromolar concentrations of 2,4-dinitrophenol (DNP) or 3-nitrophenol (NP) caused marked disaggregation of Aβ (FIG. 1C). $IC_{50}$ values of approximately 7 μM and 80 μM were found for DNP and NP, respectively. DNP (20 μM) completely abolished light scattering from Aβ suspensions, indicating complete disaggregation of fibrillar amyloid. Direct demonstration that DNP and NP inhibited aggregation of fibrillar amyloid was obtained by electron microscopy (FIG. 2).

Further results for a series of aromatic compounds are shown in Table 1, at aromatic compound concentrations of 200 micromolar.

TABLE 1

Disaggregation by Aromatic Compounds

| Compound | % decrease in light scattering |
| --- | --- |
| 2,4-dinitrophenol | 100 |
| 2-amino-4-nitrophenol | 92 |
| 3-nitrophenol | 60 |
| 2-amino-5-nitrophenol | 44 |
| 4-amino-anisole | 48 |
| 4-bromo-nitrobenzene | 37 |
| 3,4-dimethyl-phenol | 40 |
| 4-nitro-anisole | 49 |
| 2-amino-4-chlorophenol | 12 |
| 3-amino-phenol | 18 |
| 4-chloro-phenol | 20 |
| 4-bromo-phenol | 25 |
| 4-ethyl-phenol | 0 |

FIG. 2A shows an electron micrograph of control amyloid fibrils (9–10 nm diameter) obtained after aggregation of $Aβ_{1-42}$ for 2 days in PBS (Magnification: 78,750x). An $Aβ_{1-42}$ sample incubated for 2 days in the presence of 100 μM NP is shown in FIG. 2B. Inspection of a large number of EM fields failed to reveal fibrillar aggregates, with only occasional amorphous deposits present as shown in the micrograph (Magnification: 52,500x). An $Aβ_{1-42}$ sample incubated for 2 days in the presence of 20 μM DNP is shown in FIG. 2C (Magnification: 52,500x).

Abundant fibrils were observed in control samples of $Aβ_{1-42}$ (FIG. 2A), whereas samples treated with NP or DNP were completely devoid of fibrils and contained only occasional scattered amorphous aggregates (as shown in FIGS. 2B and C). Light scattering measurements indicated that nitophenol ($C_6H_5NO_3$) and dinitrophenol ($C_6H_4N_2O_5$) impede the formation of amyloid fibrils and cause dissolution of previously formed fibrils. Based on these results, it is possible to affirm that the aromatic and heteroaromatic compounds described herein destabilize the amyloid aggregates.

Example 5
Neuroprotection by Phenol Derivatives

The neuroprotective role of the phenol derivatives was evaluated in neurotoxicity assays with the β-amyloid peptide in rat embryo hippocampal neuron cultures. In order to evaluate the efficacy of the phenol derivatives, control assays were also performed in the absence of the aromatic or heteroaromatic compounds described herein.

Hippocampi from 18-day-old rat embryos were dissected and cultured as previously described by Martins et al., *Nat. Med.*, 3, 1376–82, 1997) with minor modifications. Cells were plated on glass coverslips previously coated with 1.5 μg/ml polyornithine (Sigma) in Basal Eagle's Medium (Gibco) enriched with 10% fetal calf serum (Hyclone) for the first 24 hours of culture. After that, proliferation of nonneuronal cells was inhibited with 10 μM arabinosyl cytoside and the serum concentration was lowered to 2%. $Aβ_{1-42}$ (44 μM), in the absence or in the presence of nitrophenols, was added after 48 hours of culture and kept for three days. Control cultures consisting of neurons cultured in growth medium alone or in the presence of residual TFE (0.5% v/v) were also prepared. Daily observations were carried out during this period. The overall morphology of the neurons in culture was examined by immunostaining with an anti-Tau polyclonal antibody (DAKO Corp., Carpinteria, Calif., USA), as previously described in Garcia-Abreu et al., (*J. Neurosci. Res.* 40, 471–7, 1995). Briefly, cells were washed twice with fresh medium, fixed with 4% paraformaldehyde, 4% sucrose in PBS, permeabilized with 0.1% Triton X-100 and incubated for 1 hour with anti-Tau antibody (1:200 dilution). Staining was performed by incubation with Cy3-conjugated anti-rabbit IgG (Gibco; 1:600 dilution). Fluorescence microscopy was carried out on a Zeiss Axioplan microscope.

Figure 3:
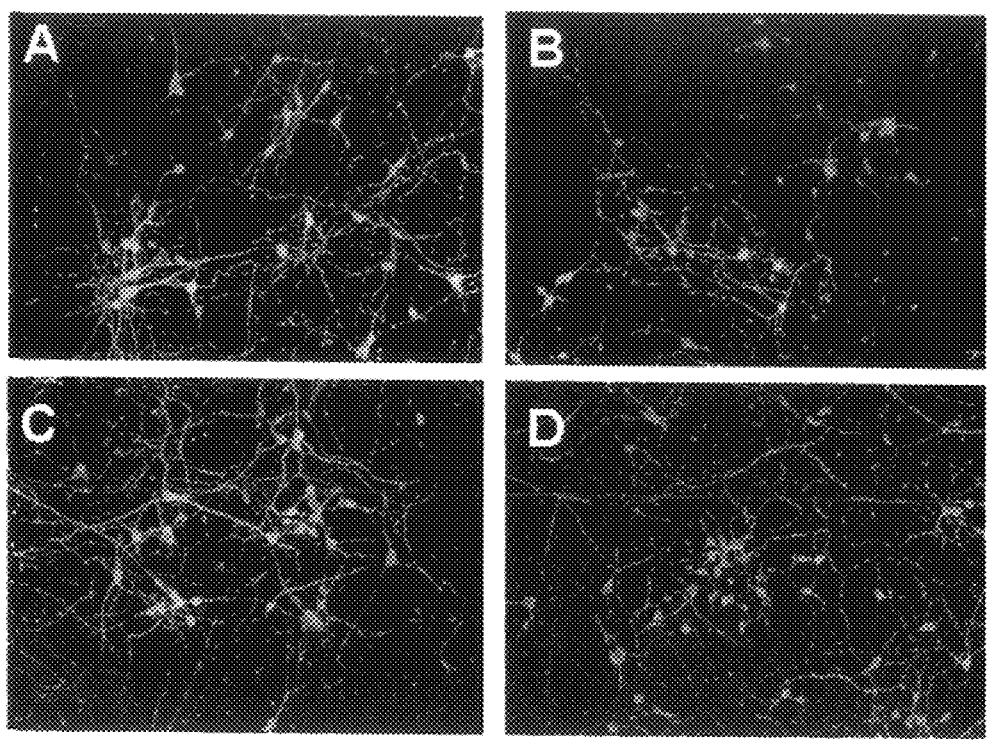
FIG. 3A is a fluorescence microscopy immunostaining of control hippocampal neurons.
FIG. 3B is a fluorescence microscopy immunostaining of hippocampal neurons in the presence of $A\beta_{1-42}$.
FIG. 3C is a fluorescence microscopy immunostaining of hippocampal neurons incubated with Aβ in the presence of 3-nitrophenol.
FIG. 3D is a fluorescence microscopy immunostaining of hippocampal neurons incubated with Aβ in the presence of 2,4-dinitrophenol.

FIG. 3 shows Aβ toxicity to cultured hippocampal neurons and protection by nitrophenols. FIG. 3A shows a control culture after 5 days in medium; FIG. 3B shows $Aβ_{1-42}$-treated culture (44 μM $Aβ_{1-42}$); FIG. 3C shows culture exposed to $Aβ_{1-42}$ (44 μM) in the presence of 100 μM NP; and FIG. 3D shows culture exposed to $Aβ_{1-42}$ (44 μM) in the presence of 20 μM DNP.

For this assay 18-day-old rat embryo hypocampal neurons were used, together with β-amyloid peptide at concentrations between 20 and 40 μM and concentrations of the aromatic and heteroaromatic compounds described herein from 20 to 100 μM.

$Aβ_{1-42}$ (44 μM) was added to the culture medium containing neurons and incubation was continued for 72 hours. Whereas control hippocampal neurons exhibited large cell bodies and long, branched neurites (FIG. 3A), significant neuronal degeneration and death was observed after 72 hours of culture in the presence of $Aβ_{1-42}$ (FIG. 3B). Large numbers of Aβ-treated neurons became detached from the plate during immunostaining washes (FIG. 3B), suggesting that neuronal adhesion was impaired. Furthermore, the remaining cell bodies of Aβ-treated neurons were attached to the plate, but their neurites were retracted and thin, and sometimes detached from the plate. Interestingly, when incubation with Aβ was carried out in the presence of NP or DNP a marked protection against neurotoxicity was observed (FIGS. 3C and 3D, respectively). In the presence of nitrophenols, neurons treated with Aβ showed large cell bodies and long neurites with good adhesion properties, and the morphological aspect of the cultures was similar to a control 5-day hippocampal culture.

Cell viability in cultures incubated with or without Aβ (as described above) was assessed by trypan blue exclusion. Immediately before counting, the medium was removed, cultures were washed once with PBS and incubated for 5 min with 0.4% trypan blue. Randomly chosen fields were counted in a Zeiss Televal microscope. Percentages of live neurons are expressed relative to the total number of neurons observed in each field. Five independent fields were counted for each experimental condition (which were carried out in triplicate). Essentially identical results were obtained in a repeat experiment using neurons from another animal.

Figure 4:
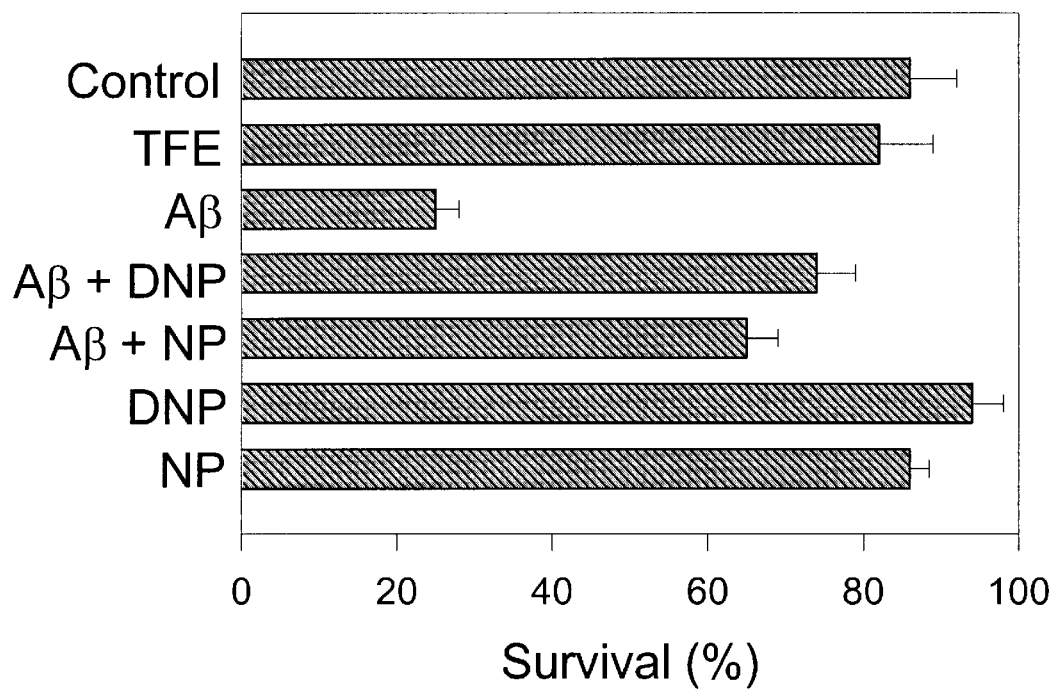
FIG. 4 is a plot of survival of hippocampal neurons upon incubation with Aβ in the absence or in the presence of nitrophenols.

Incubation of neuron cultures with β-amyloid peptide was carried out for 2–4 days. FIG. 4 shows survival of hippocampal neurons upon incubation with Aβ in the absence or in the presence of nitrophenols. Bars show averages±S.D.

(n=15) of results obtained in the absence of Aβ (control, with or without TFE), in the presence of Aβ$_{1-42}$ (44 μM), in the presence of Aβ$_{1-42}$ plus 100 μM NP or 20 μM DNP, or in the presence of nitrophenols alone, as indicated. NP or DNP by themselves or the residual concentration of TFE in the culture medium had no effects on the survival of neurons in culture. Presence of β-amyloid peptide caused 75% neuronal death, evaluated by a cell viability assay. The incubation of neurons in culture medium under identical control conditions in the absence of β-amyloid peptide (or in the presence of α-helix inducing solvent at a concentration below 0.5%) resulted in only 14–18% neuronal death. The concomitant addition of β-amyloid peptide and the aromatic or heteroaromatic compounds described herein to the cultured neurons resulted in only 26–35% cell death, indicating the protective effect of the phenol derivatives against the neurotoxicity promoted by β-amyloid peptide.

As such, it has been shown that the aromatic and heteroaromatic compounds described herein impede the aggregation of amyloid fibrils, cause the dissolution of previously formed fibrilar amyloid aggregates and protect neurons against the neurotoxicity of β-amyloid peptide. These properties, together with their defined chemical formulation, low molecular weight and permeability across biological membranes, makes the aromatic and heteroaromatic compounds described herein effective in the treatment of amyloidogenic diseases, particularly Alzheimer's disease.

Example 6
In vivo Inhibition of Amyloid Deposition

To evaluate the effects of nitrophenols as inhibitors of amyloid deposition in vivo, we used a rat model of cerebral Aβ deposition. Aβ was injected alone or in the presence of DNP into the left or right hippocampi of rats, respectively, and the areas occupied by amyloid deposits in either side were measured on consecutive sections stained with thioflavin S. The experimental protocol used was designed to minimize the influence of individual variability in animal response by injecting Aβ into one hemisphere and Aβ plus DNP into the other hemisphere for each individual rat.

Male adult Wistar rats (280–320 g) were anesthetized with chloropent (3.3 ml/kg) and placed into a stereotaxic frame. The left hippocampus (standard coordinates: A 5.0; L 2.0; H 6.8) was injected with 3 nmol of Aβ$_{1-42}$ (from a previously diluted stock in 55 μl of PBS containing 9% DMSO). A volume of 1.5 μl was administered at a constant flow rate during a time period of 15 minutes. The micropipette was left in situ for 15 min after injection, withdrawn 0.2 mm and left for 3 min, and then slowly withdrawn completely. The right hippocampus of each rat received a mixture of Aβ and DNP (0.76 mM). In this case, the concentration of DNP was increased so as to maintain approximately the same ratio of Aβ/DNP concentrations used in cell culture experiments. The animals were kept on a heating pad during surgery and until they regained their righting reflex. Animals did not receive further medication and were sacrificed 8 days later. After transcardiac perfusion with saline followed by 4% paraformaldehyde, brains were cryoprotected and frozen-cut into 20 μm thick coronal sections. Alternate sections were stained with Thioflavine-S (to reveal amyloid plaques) or cresyl violet (for inspection of cytoarchitecture), or simply dehydrated for autofluorescence examination, which provides another specific means for visualizing amyloid plaques. Sections were observed using an epifluorescence microscope (Zeiss Axioplan) and digitized with a CCD camera (Zeiss, ZVS-47EC). Images were analyzed with ScionImage to measure the areas occupied by amyloid aggregates.

Figure 5A:
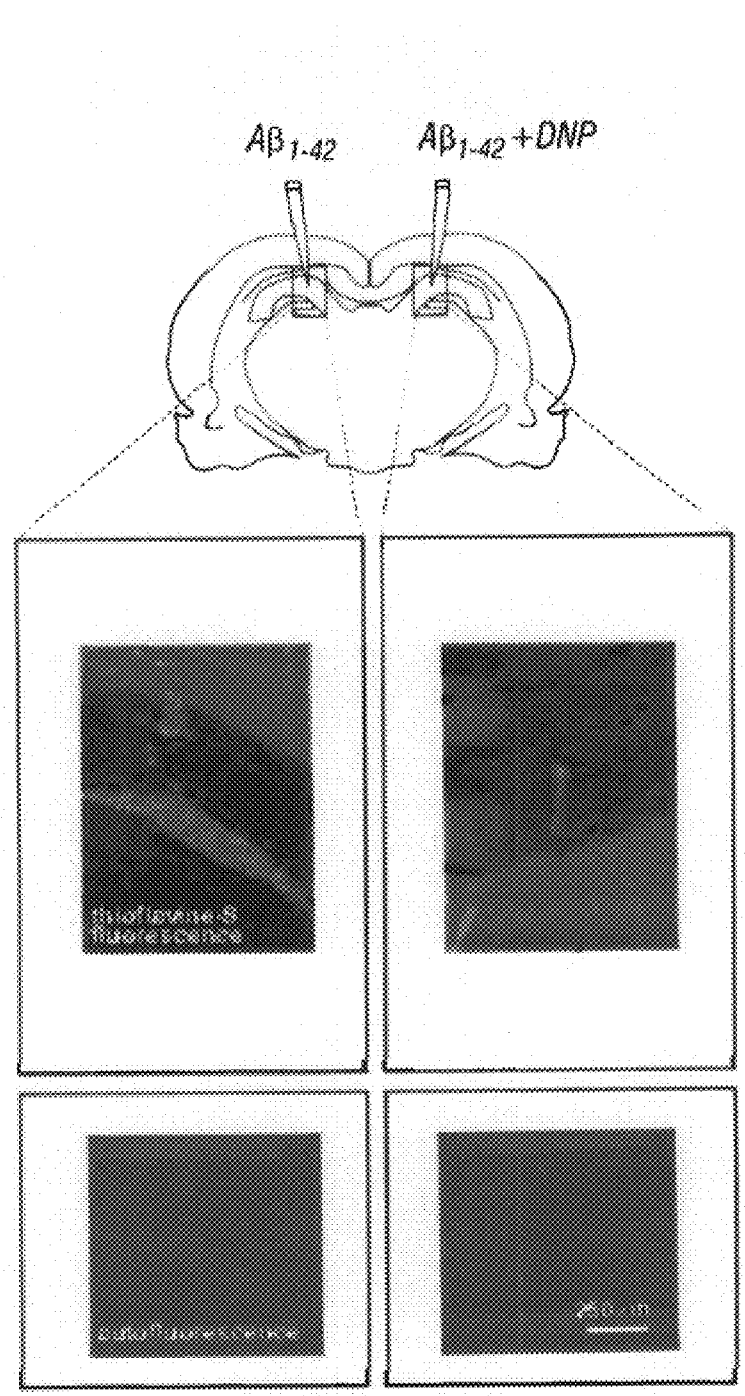
FIG. 5A is a scheme showing representative rat brain sections stained with thioflavin S or directly visualized using the autofluorescence of amyloid.

FIG. 5 shows reduction of cerebral Aβ deposition and prevention of amyloid fibril formation in vivo by DNP. FIG. 5A is a schematic diagram of the injection protocol and representative hippocampal sections visualized by Thioflavine-S staining or autofluorescence, as indicated. FIGS. 5B–5E show quantitative analysis of the area of amyloid deposits in consecutive hippocampal sections as described above. Different panels represent results obtained with different animals. Sections used for cresyl violet staining were interpolated in the image analysis. Dashed bars correspond to interpolated values. Total volumes occupied by amyloid deposits were integrated over all sections spanning the deposition region.

Co-injection of Aβ and DNP caused a reduction of 86±17% in the volume of amyloid deposits in rat brains relative to the volume occupied when Aβ was injected alone (p=0.05, n=4; one-tailed paired t-test).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for promoting the dissolution of existing amyloidoses, the method comprising administration of composition comprising a 2,4-dinitrophenol, or a pharmaceutically acceptable salt thereof, to a patient having amyloidoses in an amount sufficient to inhibit the growth of the amyloidoses or to promote the dissolution of existing amyloidoses.

2. A method for inhibiting the formation of amyloidoses, the method comprising (a) providing a composition comprising a 2,4-dinitrophenol; and (b) administering the composition to an individual having amyloidoses in an amount sufficient to inhibit the formation of amyloidoses.

3. A method for inhibiting the formation of an amyloid plaque, the method comprising (a) providing a composition comprising a 2,4-dinitrophenol; and (b) contacting the composition with an amyloid plaque, thereby inhibiting the formation of an amyloid plaque.

4. A method for inhibiting the growth of amyloidoses, the method comprising administration of composition comprising a 2,4-dinitrophenol, or a pharmaceutically acceptable salt thereof, to a patient having amyloidoses in an amount sufficient to inhibit the growth of the amyloidoses or to promote the dissolution of existing amyloidoses.

5. A method for inhibiting the growth of an amyloid plaque, the method comprising (a) providing a composition comprising a 2,4-dinitrophenol; and (b) contacting the composition with an amyloid plaque, thereby inhibiting the growth of an amyloid plaque or promoting the dissolution of an amyloid plaque.

6. A method for promoting the dissolution of an amyloid plaque, the method comprising (a) providing a composition comprising a 2,4-dinitrophenol; and (b) contacting the composition with an amyloid plaque, thereby inhibiting the growth of an amyloid plaque or promoting the dissolution of an amyloid plaque.

7. The method of claim 1 or claim 4, wherein patient has Alzheimer's Disease.

8. The method of claim 1 or claim 4, wherein patient has diabetes.

9. The method of claim 1 or claim 4, wherein patient has rheumatoid arthritis.

10. The method of claim 2, wherein individual has Alzheimer's Disease.

11. The method of claim 2, wherein individual has diabetes.

12. The method of claim 2, wherein individual has rheumatoid arthritis.

\* \* \* \* \*